United States Patent
Izawa et al.

(10) Patent No.: US 8,591,882 B2
(45) Date of Patent: Nov. 26, 2013

(54) CYTOPROTECTIVE AGENT

(75) Inventors: Naoki Izawa, Tokyo (JP); Tomoko Kurasawa, Kanagawa (JP); Toshiro Sone, Tokyo (JP); Katsuyoshi Chiba, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/819,462

(22) PCT Filed: Aug. 12, 2011

(86) PCT No.: PCT/JP2011/068424
§ 371 (c)(1),
(2), (4) Date: Feb. 27, 2013

(87) PCT Pub. No.: WO2012/026346
PCT Pub. Date: Mar. 1, 2012

(65) Prior Publication Data

US 2013/0164399 A1     Jun. 27, 2013

(30) Foreign Application Priority Data

Aug. 27, 2010   (JP) .................................. 2010-190851

(51) Int. Cl.
*A01N 63/00*     (2006.01)
*A01N 63/02*     (2006.01)
*A61K 35/00*     (2006.01)
*C12P 21/04*     (2006.01)

(52) U.S. Cl.
USPC ...................... 424/93.44; 424/780; 435/71.2

(58) Field of Classification Search
None
See application file for complete search history.

(56) References Cited

U.S. PATENT DOCUMENTS

| 6,165,982 | A | 12/2000 | Yamada et al. |
| 8,088,369 | B2 | 1/2012 | Izawa et al. |
| 2009/0317370 | A1* | 12/2009 | Lang et al. .................. 424/93.45 |
| 2010/0015110 | A1* | 1/2010 | Kano et al. .................. 424/93.44 |
| 2010/0047190 | A1* | 2/2010 | Reindl et al. ..................... 424/48 |
| 2010/0086520 | A1* | 4/2010 | Reindl et al. ................... 424/93.3 |
| 2010/0291049 | A1* | 11/2010 | Izawa et al. ................ 424/93.44 |

FOREIGN PATENT DOCUMENTS

| JP | 58 198584 | 11/1983 |
| JP | 10 140154 | 5/1998 |
| JP | 11-323328 | * 11/1999 |
| JP | 11 323328 | 11/1999 |
| JP | 3172599 | 6/2001 |
| JP | 2004 24004 | 1/2004 |
| JP | 2006 69969 | 3/2006 |
| WO | 2008 026318 | 3/2008 |

OTHER PUBLICATIONS

Ito, S., et al., "Bio Keshohin," Journal of the Toyaku, vol. 10, No. 10, pp. 13-19, (1988).
"The 7th Annual Meeting of Japanese Cosmetic Science Society," p. 59, (Jun. 3-4, 1982).
"The 8th Annual Meeting of Japanese Cosmetic Science Society," pp. 210, (Jun. 3-4, 1983).
International Search Report Issued Nov. 15, 2011 in PCT/JP11/68424 Filed Aug. 12, 2011.

* cited by examiner

*Primary Examiner* — Chris R Tate
*Assistant Examiner* — Douglas F White
(74) *Attorney, Agent, or Firm* — Oblon, Spivak, McClelland, Maier & Neustadt, L.L.P.

(57) ABSTRACT

An object of the present invention is to find a novel and useful component in a culture supernatant of a lactic acid bacterium and to provide an effective utilization method of the component. The utilization method is a cytoprotective agent containing, as an active ingredient, a low-molecular-weight fraction in a culture supernatant of a lactic acid bacterium belonging to *Streptococcus thermophilus*.

9 Claims, 1 Drawing Sheet

CYTOPROTECTIVE AGENT

CROSS REFERENCE TO RELATED APPLICATIONS

The present application is a 35 U.S.C. §371 national stage patent application of International patent application PCT/JP2011/068424, filed on Aug. 12, 2011, published as WO 2012/026346 on Mar. 1, 2012, the text of which is incorporated by reference, and claims the benefit of the filing date of Japanese application no. 2010-190851, filed on Aug. 27, 2010, the text of which is also incorporated by reference.

TECHNICAL FIELD

The present invention relates to a cytoprotective agent, and more particularly, to a cytoprotective agent containing, as an active ingredient, a low-molecular-weight fraction in a culture supernatant of a lactic acid bacterium belonging to *Streptococcus thermophilus*.

BACKGROUND ART

It has been reported that a culture supernatant of a lactic acid bacterium, i.e., a culture obtained by inoculating a lactic acid bacterium into a culture medium mainly containing milk as a principal component, contains a component having an effect as an external preparation for the skin. For example, it has been reported that a culture supernatant of a lactic acid bacterium has an antioxidative effect and a photoprotective effect (Patent Document 1, and Non-Patent Documents 1 and 2). Further, such a culture supernatant has been known to have an inhibitory effect on the formation of wrinkles (Patent Document 2), and it has also been known that in a lactic acid bacterium extract, a component having a cell proliferative effect is contained (Patent Document 3).

However, since there are a lot of lactic acid bacterial species, it is predicted that there are a wide variety of active ingredients contained in such a culture supernatant. Further, in order to use such a component as an active ingredient of a cosmetic or an external preparation, it is advantageous to select and use a portion having a particularly high activity according to the intended purpose, and therefore, it has been demanded that culture supernatants of lactic acid bacteria and lactic acid bacterial extracts be studied more to detect a component having a more potent effect.

PRIOR ART DOCUMENTS

Patent Documents

Patent Document 1: JP-A-58-198584
Patent Document 2: WO 2008/026318
Patent Document 3: Japanese Patent No. 3172599

Non-Patent Documents

Non-Patent Document 1: The 7th Annual Meeting of Japanese Cosmetic Science Society, Abstracts, 59, 1982
Non-Patent Document 2: The 8th Annual Meeting of Japanese Cosmetic Science Society, Abstracts, 210, 1983

SUMMARY OF THE INVENTION

Problems that the Invention is to Solve

Accordingly, an object of the present invention is to find a novel and useful component in a culture supernatant of a lactic acid bacterium and to provide an effective utilization method of the component.

Means for Solving the Problems

The present inventors studied active ingredients contained in culture supernatants of various lactic acid bacteria and found that in a low-molecular-weight fraction in a culture supernatant of a lactic acid bacterium belonging to *Streptococcus thermophilus*, a substance having an excellent cytoprotective effect is present, and thus completed the present invention.

That is, the present invention provides a cytoprotective agent containing, as an active ingredient, a low-molecular-weight fraction in a culture supernatant of a lactic acid bacterium belonging to *Streptococcus thermophilus*.

Further, the present invention provides an external preparation for the skin containing the cytoprotective agent.

Still further, the present invention provides a method for protecting skin cells, characterized in that a low-molecular-weight fraction in a culture supernatant of a lactic acid bacterium belonging to *Streptococcus thermophilus* is applied to the skin for the purpose of protection.

Advantage of the Invention

With the use of the cytoprotective agent of the present invention, even if cells of the skin or the like are exposed to a hydroxyl radical or the like, the cells can be protected therefrom, and skin hyperplasia, skin inflammation, skin dryness, the formation of wrinkles due to dryness, a decrease in resilience, and the occurrence and exacerbation of pigmented spots can be prevented without causing a decrease in cell number and excessive cell proliferation which occurs in succession to the decrease in cell number.

MODE FOR CARRYING OUT THE INVENTION

Figure 1:
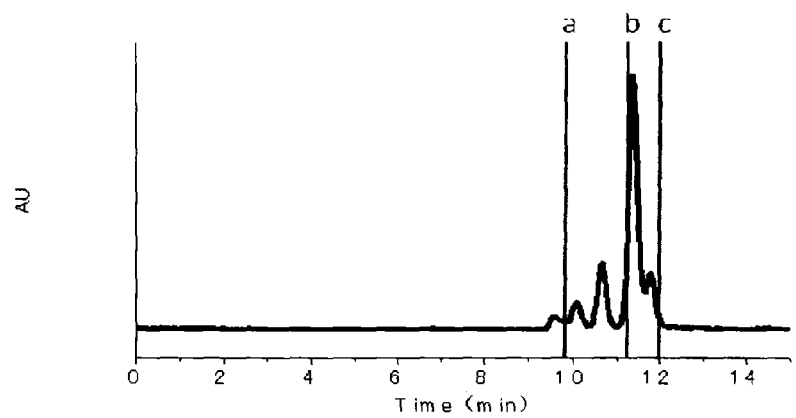
FIG. 1 is a view showing the results of HPLC of a filtrate obtained in Example 1. In the drawing, a indicates the position of molecular weight of 10,000 Da; b indicates the position of molecular weight of 342 Da; and c indicates the position of molecular weight of 180 Da.

A low-molecular-weight fraction in a culture supernatant of a lactic acid bacterium serving as an active ingredient of a cytoprotective agent of the present invention is obtained by culturing a lactic acid bacterium belonging to *Streptococcus thermophilus* in a culture medium, removing solids from the resulting culture to prepare a culture supernatant of the lactic acid bacterium, subjecting the thus prepared culture supernatant to ultrafiltration, and then, collecting a fraction with a molecular weight of 20,000 Da or less.

Examples of the lactic acid bacterium belonging to *Streptococcus thermophilus* used here include *Streptococcus thermophilus* YIT2001 strain (FERM BP-7538, deposited on Jan. 31, 2001) and *Streptococcus thermophilus* YIT2084 strain (FERM BP-10879, deposited on Aug. 18, 2006). These strains can be used alone or in combination. Incidentally, these lactic acid bacterial strains belonging to *Streptococcus thermophilus* have been deposited in the International Patent Organism Depositary, National Institute of Advanced Industrial Science and Technology (Central 6, 1-1-1 Higashi, Tsukuba-shi, Ibaraki, Japan, 305-8566).

Preferred examples of the culture medium which is used for culturing such a lactic acid bacterium belonging to *Streptococcus thermophilus* include animal milks such as human milk, cow milk, and goat milk; defatted milk; milk reconstituted from powdered milk or powdered skim milk; and dairy products such as cream. Further, processed soybean products such as soy milk can also be used, however, a culture medium containing milk as a principal component is preferred. Incidentally, such a culture medium may be used as it is, or may be used after being diluted to an adequate concentration as needed.

Moreover, to such a culture medium, a component which is generally used for the purpose of supplementing a nutrient source in the culturing of a lactic acid bacterium may be additionally added. Examples of such a component include yeast extract; chlorella extract; vitamins such as vitamin A, B vitamins, vitamin C, and E vitamins; protein degradation products including a variety of peptides; amino acids; and salts of calcium, magnesium, etc.

The culturing of the lactic acid bacterium belonging to *Streptococcus thermophilus* using any of the above-described culture media may be performed according to a common procedure. For example, the culturing is performed at a culturing temperature of from 30 to 45° C., more preferably from 37 to 42° C. for a culturing time of from 1 to 48 hours, more preferably from 4 to 24 hours. In this case, other culturing conditions include static culturing, spinner culturing, shaking culturing, aeration culturing, etc., and a method suitable for culturing may be selected from these culturing conditions and used.

The culture supernatant of the lactic acid bacterium to be used in the present invention is obtained by removing solids from the culture of the lactic acid bacterium obtained as described above according to a common procedure such as filtration, centrifugation, etc. Further, the low-molecular-weight fraction in the culture supernatant of the lactic acid bacterium can be obtained by removing a fraction with a molecular weight exceeding 20,000 Da from the culture supernatant of the lactic acid bacterium by a common procedure such as ultrafiltration or gel filtration.

The thus obtained cytoprotective agent of the present invention can suppress a decrease in cell number due to the exposure of cells to a damaging substance such as hydrogen peroxide by adding the cytoprotective agent to the cells before or during exposure of the cells to the damaging substance. However, if the cytoprotective agent is added before exposure of cells to a damaging substance, a decrease in cell number can be effectively prevented, therefore, it is preferred to add the cytoprotective agent to cells before exposure of the cells to a damaging substance.

Further, although the detailed mechanism of the above-described cytoprotective effect has not been elucidated yet, this effect is exhibited even in the case where the cytoprotective agent of the present invention does not coexist with cells when the cells are exposed to a damaging substance, and therefore, the provision of resistance to damage to the cells themselves is considered to be one of the mechanisms of the agent.

The damaging substance is not particularly limited, but examples thereof include reactive oxygen species such as a hydroxyl radical, hydrogen peroxide, singlet oxygen, and superoxide. Further, various damaging factors which induce a decrease in cell number, such as exposure to an ultraviolet ray, a radiation, a mutagenic substance, etc., stress, and smoking are also included in the damaging substance.

The cells to be targeted by the cytoprotective agent of the present invention are not particularly limited as long as they are biological cells which can be exposed to a damaging substance, but examples thereof include epidermal cells, dendritic cells, fibroblasts, mast cells, plasma cells, Langerhans cells, and vascular endothelial cells. The cytoprotective agent can be preferably used for skin cells, particularly fibroblasts among these cells.

Incidentally, *Streptococcus thermophilus* YIT2001 strain and *Streptococcus thermophilus* YIT2084 strain described above as examples of the lactic acid bacterium belonging to *Streptococcus thermophilus* to be used in the present invention are the same as those used for obtaining the culture supernatant having an inhibitory effect on the formation of wrinkles in the above-described Patent Document 2. However, the culture supernatant used in Patent Document 2 is one obtained by culturing such a lactic acid bacterium, and thereafter adding trichloroacetic acid (TCA) thereto to effect precipitation, and then, further adding ethanol thereto.

By performing TCA precipitation, proteins are removed, and further by performing ethanol extraction, polysaccharides are mainly obtained, and also low-molecular-weight components are removed. Accordingly, the culture supernatant of Patent Document 2 does not contain proteins, but contains polysaccharides having an average molecular weight of about 900,000.

On the other hand, the low-molecular-weight fraction in a culture supernatant of a lactic acid bacterium belonging to *Streptococcus thermophilus* of the invention of this application (hereinafter referred to as "culture supernatant low-molecular-weight fraction") contains proteins because TCA precipitation is not performed as described below, and also a fraction with a molecular weight of 20,000 Da or less is collected, and therefore, it is obvious that the fraction is a low-molecular-weight fraction, and the fraction is different from that of Patent Document 2 in terms of the constituent components and the molecular weights thereof.

The cytoprotective agent of the present invention contains the above-described culture supernatant low-molecular-weight fraction as an active ingredient, and as the culture supernatant low-molecular-weight fraction to be used, a fraction obtained by removing a fraction with a molecular weight exceeding 20,000 Da from the culture supernatant of the lactic acid bacterium can be used as it is, or as a liquid material after being concentrated or diluted, or as a powder material after being dried by a means such as spray drying or lyophilization.

Further, the cytoprotective agent of the present invention can be blended in an external preparation composition for the skin such as a cosmetic, a pharmaceutical, or a quasi drug. Such an external preparation composition for the skin can be produced according to a common procedure, and for example, the cytoprotective agent of the present invention may be dissolved or dispersed in purified water, a face lotion base, a cream base, a milky lotion base, or the like in an appropriate amount so that a desired effect can be exhibited.

More specific examples of the external preparation composition for the skin include basic skincare products such as face lotions, milky lotions, a variety of creams, facial masks, and serums; hair care products such as shampoos, rinses, conditioners, hair tonics, hair lotions, hair creams, and hair milks; bath products such as bath additives; makeup products such as foundations, lipsticks, mascaras, and eye shadows; and sunscreens.

The blending amount of the culture supernatant low-molecular-weight fraction as the cytoprotective agent in such an external preparation composition for the skin is not particularly limited, and may be determined according to the preparation form of the cytoprotective agent to be used or the intended use thereof, however, the blending amount thereof is from 0.01 to 100% by mass, particularly preferably from about 0.1 to 90% by mass, more preferably from 1 to 20% by mass in the case where the culture supernatant low-molecular-weight fraction is used as it is. Further, the blending amount thereof in the case where the culture supernatant low-molecular-weight fraction is used after being dried is preferably from 0.001 to 10% by mass, particularly preferably from about 0.01 to 9% by mass, more preferably from 0.1 to 2% by mass.

Further, in the above-described external preparation composition for the skin, other than the cytoprotective agent of the present invention which is contained as an essential component, an arbitrary component which is commonly blended in an external preparation for the skin can be blended. Examples of such an arbitrary component include surfactants, oils, alcohols, humectants, thickening agents, preservatives, antioxidants, chelating agents, pH adjusting agents, perfumes, dyes, UV absorbing/scattering agents, powders, vitamins, amino acids, water-soluble polymers, foaming agents, pigments, plant extracts, animal-derived components, seaweed extracts, a variety of drugs, additives, and water.

Moreover, since the cytoprotective agent of the present invention contains, as an active ingredient, a low-molecular-weight fraction in a culture supernatant of a lactic acid bacterium, which has been eaten for a long time, the agent can also be blended in a variety of foods and beverages. For example, after an appropriate auxiliary agent is added to the culture supernatant low-molecular-weight fraction, the resulting mixture may be formulated into an edible form such as a granule, a particle, a tablet, a capsule, or a paste using a common method. In addition, the mixture may be used by being added to a variety of foods, for example, processed meat products such as ham and sausage; processed fishery products such as a fish paste and a fish sausage; breads; and confectionery products, or may be used by being added to beverages such as water, fruit juice, milk, and soft drinks.

EXAMPLES

The present invention will next be described with reference to Examples, however, the present invention is by no means limited to these Examples.

Example 1

*Streptococcus thermophilus* YIT2084 strain stored at −80° C. was inoculated into MRS culture medium (Difco) in a 2-mL test tube by dipping a platinum loop in the medium once, and static culturing was performed overnight at 40° C. Subsequently, the thus obtained culture was inoculated into 2 mL of an aqueous solution of 10% powdered skim milk (10% skim milk (Difco)) to give a final concentration of 1%, and then, static culturing was performed overnight at 40° C., whereby a pre-pre-culture was prepared.

Further, pre-culturing was performed in the same manner as above, and the resulting pre-culture was inoculated into 100 mL of a culture medium (an aqueous solution of 3% powdered skim milk) for main culturing to give a final concentration of 1%, and then, static culturing was performed at 40° C. for 24 hours.

The bacterial solution after culturing was centrifuged at 8,000×g for 15 minutes at 4° C., and the precipitate was removed. The solution obtained by removing the precipitate was subjected to ultrafiltration at 3,000×g for 1 hour at 4° C. using Centricut Mini V-20 (molecular weight cut-off: 20,000 Da, Kurabo Industries Ltd.), whereby 10 mL of a filtrate 1 was obtained.

The obtained filtrate 1 was lyophilized, and the resulting lyophilized material was dissolved in 50 mM NaCl. Then, HPLC was performed for the resulting solution under the following conditions. The results are shown in FIG. 1. From the results of HPLC, it was revealed that the average molecular weight of the filtrate 1 is 300 Da.

[HPLC Conditions]
  Apparatus: Waters-600E
  Detector: ISI RI-980
  Column: Shodex SUGAR KS-804
  Column temperature: 80° C.
  Mobile phase: 50 mM NaCl
  Flow rate: 1 mL/min
  Injection amount: 10 μL Example 2

10 mL of a filtrate 2 was obtained in the same manner as in Example 1 except that *Streptococcus thermophilus* YIT2001 was used in place of *Streptococcus thermophilus* YIT2084.

Figure 2:
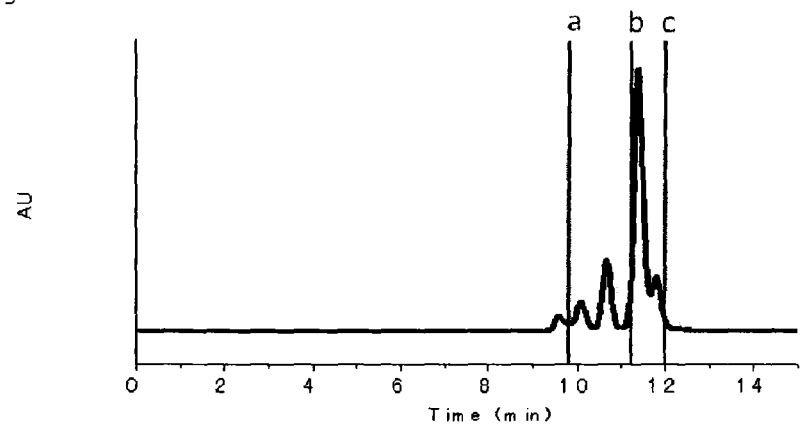
FIG. 2 is a view showing the results of HPLC of a filtrate obtained in Example 2. In the drawing, a, b, and c indicate the same as above.

HPLC was performed also for the filtrate 2 in the same manner as in Example 1, and the results as shown in FIG. 2 were obtained. It was revealed that the average molecular weight of the filtrate 2 is 300 Da.

Example 3

Exposure Test for Cells Using Hydrogen Peroxide

Mouse skin-derived fibroblasts 3T3 were inoculated into a 96-well plate at $1.3 \times 10^4$ cells/well and cultured in D-MEM culture medium containing 10% FBS in a 5% $CO_2$ atmosphere at 37° C. for 24 hours.

After culturing, the culture medium was removed and the cells were washed twice with PBS, and then, the culture medium was replaced with D-MEM culture medium (100 μL). 10 μl of each of the filtrate 1, the filtrate 2, and solutions obtained by diluting these filtrates to 2-fold with PBS was added to each well of the plate, and the plate was incubated in a 5% $CO_2$ atmosphere at 37° C. for 24 hours. As the filtrates, filtrates each obtained by removing a fraction having a molecular weight exceeding 20,000 Da from the culture supernatant of the lactic acid bacterium were used as it is.

The culture medium was removed again, and the cells were washed twice with PBS. Then, $H_2O_2$ and $FeSO_4$ were added to each well to give a final concentration of 400 μM and 5 μM, respectively, and the plate was incubated in a 5% $CO_2$ atmosphere at 37° C. for 6 hours. In a non-exposure group, only PBS was added to a well, and the plate was incubated in the same conditions.

Finally, the cells were stained with crystal violet, and the absorbance at 590 nm was used as an index of a viable cell number. Incidentally, in control group, instead of the filtrate, PBS was used. The results are shown in Table 1.

TABLE 1

|  |  | Absorbance at 590 nm |
|---|---|---|
| Exposure to hydrogen peroxide | Undiluted filtrate 1 | 0.053 |
|  | 2-Fold dilution of filtrate 1 | 0.035 |
|  | Undiluted filtrate 2 | 0.043 |
|  | 2-Fold dilution of filtrate 2 | 0.036 |
|  | Control (PBS) | 0.023 |
| Non-exposure to hydrogen peroxide | Undiluted filtrate 1 | 0.051 |
|  | Undiluted filtrate 2 | 0.064 |
|  | Control (PBS) | 0.031 |

As described above, by the addition of the filtrate 1 or 2, the absorbance at 590 nm was increased in a concentration-dependent manner, and therefore, it was revealed that the filtrates 1 and 2 have a cytoprotective effect. Further, when a comparison of the ratio of the viable cells was made between the case where the cells were exposed to hydrogen peroxide and the case where the cells were not exposed to hydrogen peroxide (non-exposure), it was 1.04 times in the case of the filtrate 1, and the cell number was not decreased even by the exposure to hydrogen peroxide.

Example 4

Scavenging Effect on Hydrogen Peroxide

To a 50 μM $H_2O_2$ solution, each of the filtrate 1, the filtrate 2, and diluted solutions obtained by diluting these filtrates to 2-, 4-, and 8-fold with PBS was added, and then, the resulting solutions were incubated at 37° C. for 30 minutes. Thereafter, the concentration of $H_2O_2$ was measured. The results are shown in Table 2.

TABLE 2

|  | Concentration of $H_2O_2$ (μM) | |
|---|---|---|
|  | Filtrate 1 | Filtrate 2 |
| Undiluted | 15.38 | 16.02 |
| 2-Fold dilution | 17.94 | 20.06 |
| 4-Fold dilution | 27.09 | 26.02 |
| 8-Fold dilution | 34.32 | 33.68 |
| No addition | 47.30 | 47.30 |

From the above results, the effect of the filtrate 1 on hydrogen peroxide is substantially the same as that of the filtrate 2. Therefore, it was indicated that the effect of the filtrate 1 observed in the above-described Example 3 is attributed not to the scavenging of hydrogen peroxide, but to another mechanism.

Example 5

Preparation of Face Lotion

A face lotion was prepared according to the following formulation. As for the preparation method, materials (7) and (6) were mixed, and materials (1) to (5) were added thereto, and then, the resulting mixture was sufficiently stirred, whereby a face lotion was obtained. As the filtrate 1, a culture supernatant low-molecular-weight fraction was used as it is.

TABLE 3

|  | Raw materials | Using amount (% by mass) |
|---|---|---|
| (1) | Ethanol | 5.0 |
| (2) | 1,3-Butylene glycol | 2.0 |
| (3) | Polyoxyethylene hydrogenated castor oil | 0.05 |
| (4) | Methyl parahydroxybenzoate | 0.1 |
| (5) | Perfume | 0.1 |
| (6) | Filtrate 1 | 3.0 |
| (7) | Distilled water | Amount to make the total 100 |

Example 6

Preparation of Milky Lotion

A milky lotion was prepared according to the following formulation. As for the preparation method, materials (7), (8), and (10) were added to material (11), and the resulting mixture was heated. Then, materials (1) to (6) were added thereto at 80° C., followed by emulsification. Thereafter, material (9) was added thereto, and the resulting mixture was stirred, and then, cooled to room temperature, whereby a milky lotion was obtained. As the filtrate 1, a culture supernatant low-molecular-weight fraction was used as it is.

TABLE 4

|  | Raw materials | Using amount (% by mass) |
|---|---|---|
| (1) | Stearic acid | 2.0 |
| (2) | Liquid paraffin | 5.0 |
| (3) | Squalane | 2.0 |
| (4) | Sorbitan monostearate | 0.05 |
| (5) | Polyoxyethylene (20) sorbitan monostearate | 2.0 |
| (6) | Butyl parahydroxybenzoate | 0.05 |
| (7) | Glycerin | 2.0 |
| (8) | Methyl parahydroxybenzoate | 0.1 |
| (9) | Perfume | 0.15 |
| (10) | Filtrate 1 | 5.0 |
| (11) | Distilled water | Amount to make the total 100 |

Example 7

Preparation of Cream

A cream was prepared according to the following formulation. As for the preparation method, materials (9), (10), (12), and (13) were added to material (14), and the resulting mixture was heated. Then, materials (1) to (8) were added thereto at 80° C., followed by emulsification. Thereafter, material (11) was added thereto, and the resulting mixture was stirred, and then, cooled to room temperature, whereby a cream was obtained. As the filtrate 1, a culture supernatant low-molecular-weight fraction was used as it is.

TABLE 5

|  | Raw materials | Using amount (% by mass) |
|---|---|---|
| (1) | Liquid paraffin | 23.0 |
| (2) | Petrolatum | 7.0 |
| (3) | Cetanol | 1.0 |
| (4) | Stearic acid | 2.0 |
| (5) | Beeswax | 2.0 |
| (6) | Sorbitan monostearate | 3.5 |
| (7) | Polyoxyethylene (20) sorbitan monostearate | 2.5 |
| (8) | Butyl parahydroxybenzoate | 0.05 |

TABLE 5-continued

| | Raw materials | Using amount (% by mass) |
|---|---|---|
| (9) | 1,3-Butylene glycol | 1.0 |
| (10) | Methyl parahydroxybenzoate | 0.1 |
| (11) | Perfume | 0.15 |
| (12) | Lactic acid bacterial culture solution | 5.0 |
| (13) | Filtrate 1 | 1.0 |
| (14) | Distilled water | Amount to make the total 100 |

INDUSTRIAL APPLICABILITY

As shown in the above-described Examples, the cytoprotective agent of the present invention has a function to protect cells from a damaging substance such as hydrogen peroxide. If cells are protected and the cell number is maintained, sufficient intercellular lipids are formed, and the barrier function of a horny cell layer is sufficiently exhibited, thereby preventing the loss of water. Therefore, the content of water is increased to improve skin roughness, and so on. Further, since the cell number decreases as aging progresses, the cytoprotective agent of the present invention is expected to also exhibit an anti-aging effect.

As described above, the cytoprotective agent of the present invention has an effect of protecting cells from a damaging substance such as hydrogen peroxide, and therefore can be used as a useful component to be blended in an external preparation for the skin and a cosmetic.

Further, a low-molecular-weight fraction in a culture supernatant of a lactic acid bacterium belonging to *Streptococcus thermophilus* serving as an active ingredient of the cytoprotective agent has an effect of protecting cells from a damaging substance as described above. Therefore, by applying the low-molecular-weight fraction to the skin to be protected, for example, epidermis including horny and basal layers and so on, dermis, etc., skin cells can be protected.

The invention claimed is:

1. A cytoprotective agent comprising, as an active ingredient, a low-molecular-weight fraction of a culture supernatant of *Streptococcus thermophilus* YIT2084 strain (FERM BP-10879), wherein the low-molecular-weight fraction has a molecular weight of 20,000 Da or less, wherein a decrease in cell number when cells are exposed to a damaging substance is suppressed, and wherein the low molecular weight fraction is produced by a method comprising:

culturing the *Streptococcus thermophilus* YIT2084 strain (FERM BP-10879) in a culture medium;
obtaining a culture supernatant from the cultured medium;
subjecting the culture supernatant to ultrafiltration or gel filtration to obtain the low-molecular-weight fraction.

2. The cytoprotective agent of claim 1, wherein the damaging substance is a reactive oxygen species.

3. The cytoprotective agent of claim 1, wherein the damaging substance is a hydroxyl radical.

4. An external preparation comprising an effective amount of the cytoprotective agent of claim 1.

5. The external preparation of claim 4, wherein the preparation is a cosmetic.

6. A method for protecting skin cells, the method comprising:

applying an effective amount of a low-molecular-weight fraction obtained from a culture supernatant of *Streptococcus thermophilus* YIT2084 strain (FERM BP-10879) to the skin of a subject in need thereof, wherein the low-molecular-weight fraction has a molecular weight of 20,000 Da or less, wherein a decrease in cell number when cells are exposed to a damaging substance is suppressed, and wherein the low molecular weight fraction is produced by a method comprising:
culturing the *Streptococcus thermophilus* YIT2084 strain (FERM BP-10879) in a culture medium;
obtaining a culture supernatant from the cultured medium, and
subjecting the culture supernatant to ultrafiltration or gel filtration to obtain the low-molecular-weight fraction.

7. A method of producing a cytoprotective agent, the method comprising:

culturing a *Streptococcus thermophilus* YIT2084 strain (FERM BP-10879) in a culture medium;
removing solids from the cultured medium to obtain a culture supernatant of the lactic acid bacterium; and
subjecting the culture supernatant to ultrafiltration or gel filtration to obtain a low-molecular-weight fraction having a molecular weight of 20,000 Da or less; wherein the cytoprotective agent suppresses a decrease in cell number when cells are exposed to a damaging substance.

8. The method of claim 6, wherein the damaging substance is a reactive oxygen species.

9. The method of claim 6, wherein the damaging substance is a hydroxyl radical.

* * * * *